(12) United States Patent
Gaitonde et al.

(10) Patent No.: US 8,288,401 B2
(45) Date of Patent: Oct. 16, 2012

(54) POLYMORPHIC FORMS

(75) Inventors: Abhay Gaitonde, Maharashtra (IN);
Bindu Manojkumar, Maharashtra (IN);
Sandeep Mekde, Maharashtra (IN);
Dattaatraya Shinde, Maharashtra (IN);
Prakash Bansode, Maharashtra (IN)

(73) Assignee: Generics [UK] Limited, Hertfordshire (GB)

( * ) Notice: Subject to any disclaimer, the term of this patent is extended or adjusted under 35 U.S.C. 154(b) by 0 days.

(21) Appl. No.: 12/599,108

(22) PCT Filed: May 8, 2008

(86) PCT No.: PCT/GB2008/050338
§ 371 (c)(1),
(2), (4) Date: Jun. 2, 2010

(87) PCT Pub. No.: WO2008/135795
PCT Pub. Date: Nov. 13, 2008

(65) Prior Publication Data
US 2010/0261742 A1 Oct. 14, 2010

(30) Foreign Application Priority Data

May 8, 2007 (IN) .......................... 881/MUM/2007

(51) Int. Cl.
*A01N 43/54* (2006.01)
*A61K 31/505* (2006.01)
(52) U.S. Cl. ........................................ 514/269; 544/296
(58) Field of Classification Search .................... 544/296
See application file for complete search history.

(56) References Cited

U.S. PATENT DOCUMENTS 5,292,740 A 3/1994 Burri et al.
2010/0331352 A1* 12/2010 Gaitonde ...................... 514/269

FOREIGN PATENT DOCUMENTS

WO WO 01/55120 8/2001
WO WO 0155120 A1 * 8/2001

OTHER PUBLICATIONS

S.L. Morissette et al., Advanced Drug Delivery Reviews, 56, 275-300 (2004).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
Harada Hironori et al., "Ethenesulfonamide and Ethanesulfonamide Derivatives, a Novel Class of Orally Active Endotheline-A Receiptor Antagonists", Bioorganic & Medicinal Chemistry, Elsevies Scient Ltd., GB, vol. 9, Jan. 1, 2001, pp. 2955-2968, XP002238534, ISSN: 0968-0896.
Yang, Ning et al., "Synthesis of Bosentan as an Endotehlin Receptor Antagonist", Zhongguo Yaowu Huaxue Zazhi—Chinese Journal of Medicinal Chemistry, GAI-KAI Bianjibu, Shenyang, CN, vol. 15, No. 4, Jan. 1, 2005, pp. 230-233, XP008096375, ISSN: 1005-0108.
International Search Report PCT/GB2008/050338, 6 pgs.

* cited by examiner

*Primary Examiner* — James O Wilson
*Assistant Examiner* — Alexander R Pagano
(74) *Attorney, Agent, or Firm* — Scott D. Rothenberger; Fulbright & Jaworski L.L.P.

(57) ABSTRACT

Novel polymorphic forms of bosentan and processes for their preparation are disclosed. Further, pharmaceutical compositions comprising said polymorphic forms and the use of said compositions in the treatment of patients suffering from endothelin receptor mediated disorders, for example, cardiovascular disorders such as hypertension, pulmonary hypertension, ischemia, vasospasm and angina pectoris are disclosed.

16 Claims, 7 Drawing Sheets

POLYMORPHIC FORMS

CROSS-REFERENCE TO RELATED APPLICATION(S)

Figure 1:
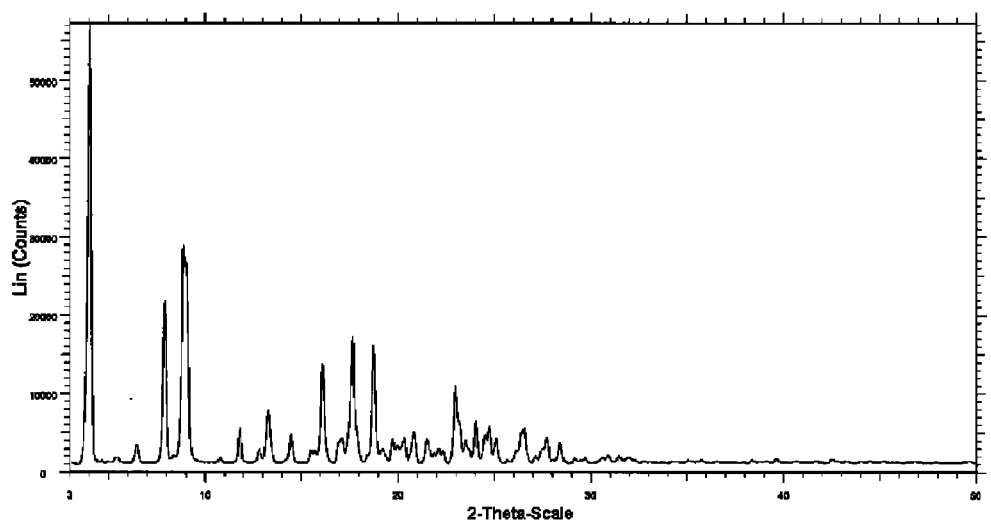

This application is a Section 371 National Stage Application of International No. PCT/GB2008/050338, filed 8 May 2008 and published as WO 2008/135795 A3 on 13 Nov. 2008, which claims priority from the India Application 881/mum/2007, filed 8 May 2007, the contents of which are incorporated herein in their entirety for all purposes.

FIELD OF THE INVENTION

The present invention relates to novel polymorphic forms of bosentan and to processes for their preparation. Further, the invention relates to pharmaceutical compositions comprising said polymorphic forms and the use of said compositions in the treatment of patients suffering from endothelin receptor mediated disorders, for example, cardiovascular disorders such as hypertension, pulmonary hypertension, ischemia, vasospasm and angina pectoris.

BACKGROUND OF THE INVENTION

Bosentan, represented by structural formula (I) and chemically named N-[6-(2-hydroxyethoxy)-5-(2-methoxyphenoxy)-2-(2-pyrimidinyl)-pyrimidin-4-yl]-4-tert-butyl-benzenesulfonamide, is an endothelin receptor antagonist. It is useful for the treatment of cardiovascular disorders such as hypertension, ischemia, vasospasm and angina pectoris and the marketed product, Tracleer®, is indicated for the treatment of pulmonary arterial hypertension (PAH) to improve exercise capacity and symptoms in patients with grade III functional status.

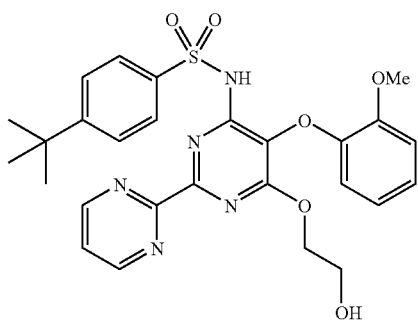

(I)

Bosentan was first described in U.S. Pat. No. 5,292,740. The preparation method involves coupling of N-[6-chloro-5-(2-methoxyphenoxy)-2-(2-pyrimidinyl)-pyrimidin-4-yl]-4-tert-butyl-benzenesulfonamide and sodium ethylene glycolate in ethylene glycol at 100° C. However, one of the disadvantages of this process is the formation of undesired ethylene glycol bis-sulfonamide in which two molecules of the pyrimidine monohalide are coupled with one molecule of ethylene glycol. The removal of this impurity requires costly and laborious separation steps. To minimize the formation of this impurity a large excess of ethylene glycol is used which again is impractical on a large industrial scale. The process disclosed in patent application WO 01/55120 has overcome the above problems by using protected ethylene glycol for the reaction.

Polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different X-ray diffraction peaks. Since the solubility of each polymorph may vary, identifying the existence of pharmaceutical polymorphs is essential for providing pharmaceuticals with predictable solubility profiles. Polymorphic forms of a compound can be distinguished by X-ray diffraction spectroscopy and by other methods such as infrared spectrometry. Additionally, the properties of polymorphic forms of the same active pharmaceutical ingredient are well known in the pharmaceutical art to have an effect on the manufacture of drug product compositions comprising the active pharmaceutical ingredient. For example, the solubility, stability, flowability, tractability and compressibility of the active pharmaceutical ingredient as well as the safety and efficacy of the drug product can be dependent on the crystalline from.

The discovery of new polymorphic forms of a pharmaceutically useful compound provides a new opportunity to improve the performance characteristics of the pharmaceutical product. It also adds to the choice that a formulation scientist has available for designing, for example, a pharmaceutical dosage form of a drug with a targeted release profile or other desired characteristics.

SUMMARY OF THE INVENTION

Novel polymorphic forms of bosentan have been prepared and characterised, and processes for their preparation are described below. The novel polymorphic forms of bosentan have been found to have advantageous properties, for example, better solubility, bioavailability, stability, flowability, tractability or compressibility.

Accordingly, a first aspect of the present invention provides a crystalline form of bosentan designated form 1 comprising at least five, six, seven, eight or nine characteristic X-ray diffraction peaks selected from peaks at 2θ values 3.9, 7.8, 8.8, 13.2, 16.1, 17.6, 18.7, 23.0 and 24.0±0.2, preferably selected from peaks at 2θ values 3.94, 7.84, 8.84, 13.23, 16.10, 17.63, 18.74, 22.98 and 24.01±0.2.

Figure 2:
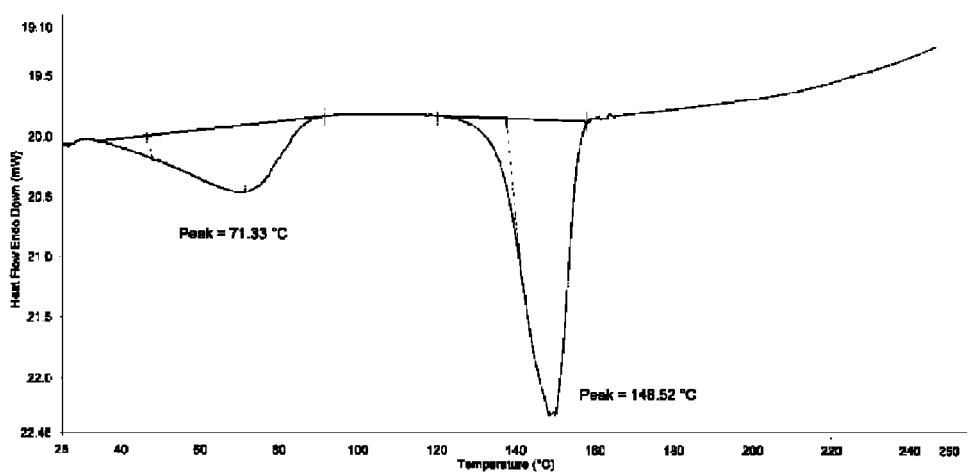

In a second aspect of the invention, crystalline form 1 of bosentan is characterized by a DSC comprising an endotherm at about 148° C. Preferably the crystalline form 1 of bosentan has a DSC substantially as depicted in FIG. 2.

Preferably the crystalline form 1 of bosentan of the present invention is substantially free of other polymorphic forms including amorphous bosentan. It preferably comprises less than 5%, preferably less than 3%, preferably less than 2%, preferably less than 1%, preferably less than 0.5%, preferably less than 0.1% of other polymorphic forms including amorphous bosentan.

In a third aspect, crystalline form 1 of bosentan is prepared by a process according to the invention comprising the steps of:

(a) dissolving bosentan in one or more organic solvent(s),
(b) causing a crystalline solid to precipitate from the solution obtained in step (a), and
(c) isolating the crystalline solid obtained in step (b).

In a preferred embodiment of the process, the organic solvent(s) in step (a) is/are selected from tetrahydrofuran, isobutanol, and ethanol. In another embodiment of the process, the crystalline solid is caused to precipitate by the addition of an anti-solvent. Preferably when the organic solvent is tetrahydrofuran or isobutanol the anti-solvent is n-hexane, and when the organic solvent is ethanol the anti-solvent is water. In a further embodiment of the process, in step (a) the organic solvent(s) is/are heated until at least 40%, preferably at least 60%, more preferably at least 80% of the bosentan is dissolved in the organic solvent(s). In a further embodiment of the third aspect, a process is provided wherein the bosentan is dissolved in the organic solvent(s) by heating the organic solvent(s) to a temperature that facilitates the bosentan dissolving. Preferably the solution obtained in step (a) is filtered. In another embodiment, an anti-solvent is added to the filtrate, the anti-solvent is preferably n-hexane. In another embodiment, in step (c) the crystalline solid is isolated by filtration. Preferably the isolated crystalline solid is dried, most preferably air-dried.

A fourth aspect of the invention provides a process for preparing crystalline form 1 of bosentan by:
(a) heating bosentan in isobutanol until a clear solution is obtained,
(b) preferably cooling the solution obtained in step (a),
(c) preferably filtering the solution obtained in step (a) or (b),
(d) adding one or more anti-solvent(s) to the solution obtained in step (a) or (b) or to the filtrate obtained in step (c),
(e) isolating the crystalline solid obtained in step (d), and
(f) preferably drying the crystalline solid obtained in step (e).

In one embodiment of a process according to the fourth aspect, the bosentan is heated in the isobutanol to about 70-100° C., preferably to about 90° C. In another embodiment, the solution in step (b) is cooled to about 10-50° C., preferably the solution is cooled to about 30° C. In another embodiment, the anti-solvent used in step (d) is n-hexane. In a preferred embodiment, in step (e) the crystalline solid is isolated by filtration. According to another embodiment, in step (f) the crystalline solid is air-dried, preferably for about 12 hours.

In a fifth aspect, there is provided a process for preparing crystalline bosentan form 1 comprising the steps of:
(a) dissolving bosentan in tetrahydrofuran at room temperature until a clear solution is obtained,
(b) adding one or more anti-solvent(s) to the solution obtained in step (a),
(c) isolating the crystalline solid obtained in step (b), and
(d) preferably drying the crystalline solid obtained in step (c).

In a preferred embodiment, room temperature is about 20-25° C. In a preferred embodiment, the anti-solvent used in step (b) is n-hexane. In another embodiment, in step (c) the crystalline solid is isolated by filtration. In a further embodiment, in step (d) the crystalline solid is dried under vacuum.

In a sixth aspect according to the invention, there is provided a novel crystalline form 2 of bosentan characterized by an X-ray diffraction pattern comprising at least five, six, seven, eight or nine peaks selected from peaks at 2θ values 7.6, 13.6, 16.6, 16.9, 17.3, 18.6, 20.0, 20.3 and 23.0±0.2.

Figure 5:
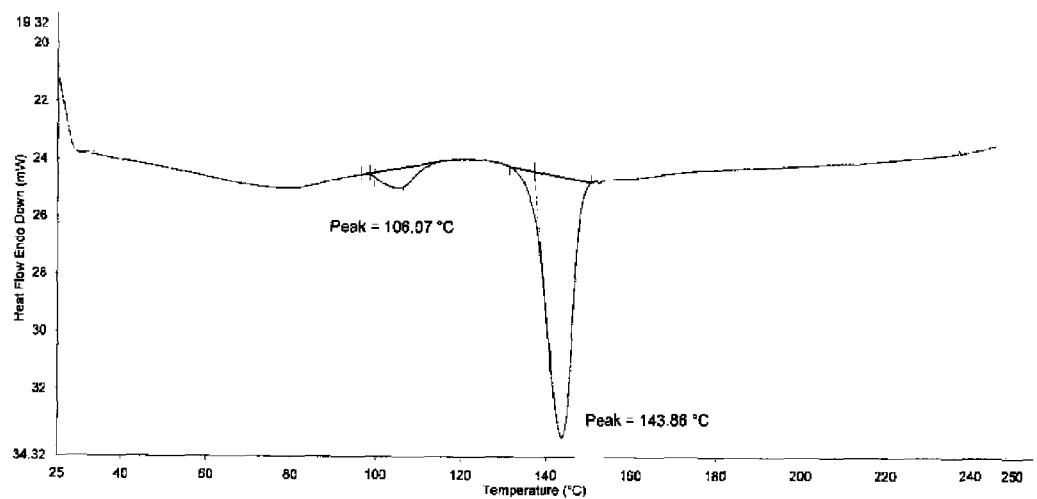

In a seventh aspect of the invention, crystalline form 2 of bosentan is characterized by a DSC comprising an endotherm at about 144° C. Preferably the crystalline form 2 of bosentan has a DSC substantially as depicted in FIG. 5.

Preferably the crystalline form 2 of bosentan of the present invention is substantially free of other polymorphic forms including amorphous bosentan. It preferably comprises less than 5%, preferably less than 3%, preferably less than 2%, preferably less than 1%, preferably less than 0.5%, preferably less than 0.1% of other polymorphic forms including amorphous bosentan.

An eighth aspect according to the invention provides a process for the preparation of the crystalline form 2 comprising the steps of:
(a) dissolving bosentan in one or more organic solvent(s),
(b) causing a crystalline solid to precipitate from the solution obtained in step (a), and
(c) isolating the crystalline solid obtained in step (b).

In a preferred embodiment, the organic solvent(s) in step (a) is/are selected from n-butanol, 2-ethoxyethanol, n-propyl acetate, and 2-methoxyethanol. Preferably at least 40%, more preferably at least 60%, most preferably at least 80% of the bosentan is dissolved in the organic solvent(s).

In a particularly preferred embodiment, the organic solvent in step (a) is n-butanol. Preferably at least 40%, more preferably at least 60%, most preferably at least 80% of the bosentan is dissolved in the n-butanol. In another embodiment, the bosentan is dissolved by heating the n-butanol preferably to about 60-100° C., most preferably the n-butanol is heated to about 90° C. In a further embodiment still, in step (b) the crystalline solid is caused to precipitate by adding one or more anti-solvent(s). Preferably the anti-solvent is n-hexane.

In another preferred embodiment, the organic solvent in step (a) is 2-ethoxyethanol. Preferably at least 40%, more preferably at least 60%, most preferably at least 80% of the bosentan is dissolved in the 2-ethoxyethanol. In another embodiment, the bosentan is dissolved by heating the 2-ethoxyethanol preferably to about 30-70° C., most preferably the 2-ethoxyethanol is heated to about 45° C. In a further embodiment still, in step (b) the crystalline solid is caused to precipitate by adding one or more anti-solvent(s). Preferably the anti-solvents are n-hexane and water.

In yet another preferred embodiment, the organic solvent in step (a) is 2-methoxyethanol. Preferably at least 40%, more preferably at least 60%, most preferably at least 80% of the bosentan is dissolved in the 2-methoxyethanol. In another embodiment, the bosentan is dissolved by heating the 2-methoxyethanol preferably to about 35-70° C., most preferably the 2-methoxyethanol is heated to about 45° C. In a further embodiment still, the crystalline solid is caused to precipitate by cooling the solution obtained in step (a). Preferably the solution is cooled to about 10-30° C., most preferably the solution is cooled to about 25° C.

In a further aspect according to the invention, there is provided a process for preparing form 2 of bosentan comprising the steps of:
(a) heating bosentan in n-butanol to about 60-100° C., preferably to about 90° C.,
(b) preferably cooling the solution obtained in step (a) to about 10-30° C. over about 0.5-3 hours, preferably to about 25° C. over about 60 minutes,
(c) preferably filtering the solution obtained in step (a) or (b),
(d) adding n-hexane to the solution obtained in step (a) or (b) or to the filtrate obtained in step (c) to precipitate a crystalline solid,
(e) isolating the crystalline solid obtained in step (d) by filtration, and
(f) preferably air-drying the crystalline solid obtained in step (e) for about 2-48 hours, preferably for about 12 hours.

In a further aspect, a process for preparing form 2 of bosentan is provided comprising the steps of:
(a) heating bosentan in 2-ethoxyethanol to about 30-70° C., preferably to about 45° C.,
(b) preferably cooling the solution obtained in step (a) to about 5-15° C. over about 0.5-3 hours, preferably to about 10° C. over about 50 minutes,
(c) adding n-hexane and water to the solution obtained in step (a) or (b) to precipitate a crystalline solid,
(d) isolating the crystalline solid obtained in step (c) by filtration, and (e) preferably air-drying the crystalline solid obtained in step (d) for about 2-48 hours, preferably for about 12 hours.

A further aspect provides a process for preparing form 2 of bosentan comprising the steps of:
(a) heating bosentan in n-propyl acetate to about 70-90° C., preferably to about 80° C.,
(b) cooling the solution obtained in step (a) to about 10-30° C., preferably to about 25° C., to precipitate a crystalline solid,
(c) isolating the crystalline solid obtained in step (b) by filtration, and
(d) preferably air-drying the crystalline solid obtained in step (c) for about 2-48 hours, preferably for about 12 hours.

A further aspect provides a process for preparing form 2 of bosentan comprising the steps of:
(a) heating bosentan in 2-methoxyethanol to about 35-70° C., preferably to about 45° C., or until a clear solution is obtained,
(b) preferably cooling the solution obtained in step (a) to about 10-30° C., preferably to about 25° C.,
(c) adding water to the solution obtained in step (a) or (b) to precipitate a crystalline solid,
(d) isolating the crystalline solid obtained in step (c) by filtration, and
(e) preferably air-drying the crystalline solid obtained in step (d) for about 2-48 hours, preferably for about 12 hours.

A further aspect provides a crystalline form 3 of bosentan characterized by an X-ray diffraction pattern comprising at least five, six, seven, eight or nine peaks selected from peaks at 2θ values 5.2, 7.5, 8.2, 9.3, 10.0, 18.1, 20.5, 21.5 and 25.0±0.2.

Figure 8:
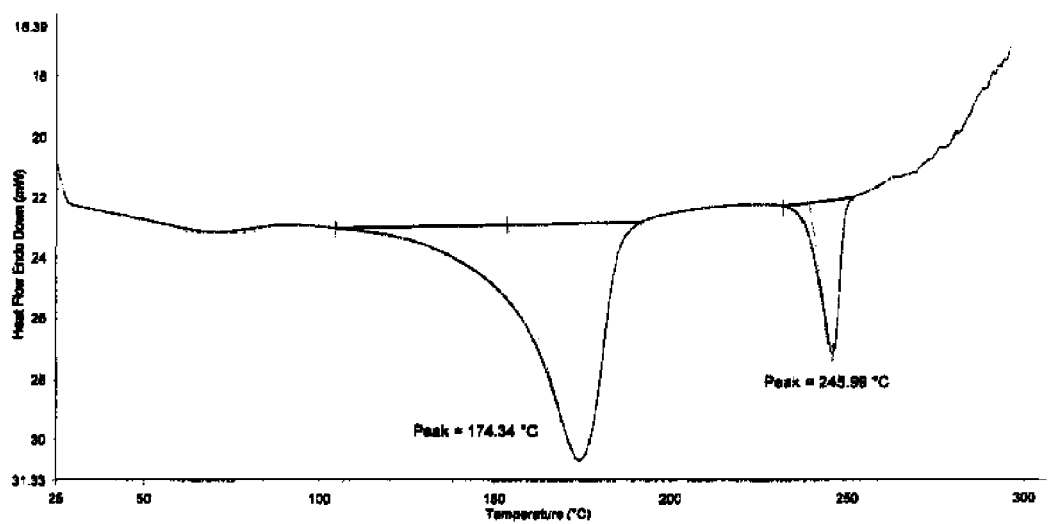

In a further aspect of the invention, crystalline form 3 of bosentan is characterized by a DSC comprising an endotherm at about 174° C. and an endotherm at about 246° C. Preferably the crystalline form 3 of bosentan has a DSC substantially as depicted in FIG. 8.

Preferably the crystalline form 3 of bosentan of the present invention is substantially free of other polymorphic forms including amorphous bosentan. It preferably comprises less than 5%, preferably less than 3%, preferably less than 2%, preferably less than 1%, preferably less than 0.5%, preferably less than 0.1% of other polymorphic forms including amorphous bosentan.

In a further aspect, there is provided a process for preparing crystalline form 3 of bosentan comprising the steps of:
(a) dissolving bosentan in one or more organic solvent(s),
(b) causing a crystalline solid to precipitate from the solution obtained in step (a), and
(c) isolating the crystalline solid obtained in step (b).

In one embodiment, the organic solvent(s) comprise(s) an alcoholic solvent, preferably a straight or branched chain $C_1$-$C_6$ alcohol. In a particularly preferred embodiment, the organic solvent(s) is/are selected from n-pentanol, isoamyl alcohol, cyclohexanol, n-propanol, n-butanol, cyclopentanol, and isobutanol. Alternatively, the organic solvent is cyclohexane or toluene. In another preferred embodiment, the organic solvent in step (a) is 2-ethoxyethanol. Preferably at least 40%, more preferably at least 60%, most preferably at least 80% of the bosentan is dissolved in the organic solvent(s).

In another embodiment, the bosentan is dissolved by heating the organic solvent(s), preferably to about 35-100° C., preferably to about 40-100° C., preferably to about 60-100° C., preferably to about 60-90° C. In a further embodiment a co-solvent, preferably dichloromethane, is added to dissolve the bosentan. In a further embodiment still, in step (b) the crystalline solid is caused to precipitate by adding an anti-solvent. In a particularly preferred embodiment, when the organic solvent is n-pentanol the anti-solvent is n-hexane, or alternatively when the solvent is toluene the anti-solvent is water. Alternatively, the crystalline solid is caused to precipitate by cooling the solution obtained in step (a), preferably the solution is cooled to about 5-30° C.

In another embodiment, in step (c) the crystalline solid is isolated by filtration and preferably the crystalline solid is dried under vacuum or alternatively the crystalline solid is air-dried.

A further aspect of the invention relates to crystalline form 4 of bosentan characterized by an X-ray diffraction pattern comprising at least five, six, seven, eight or nine peaks selected from peaks at 2θ values 5.7, 6.4, 9.5, 15.6, 16.6, 21.2, 21.5, 27.4 and 31.8±0.2.

Figure 11:
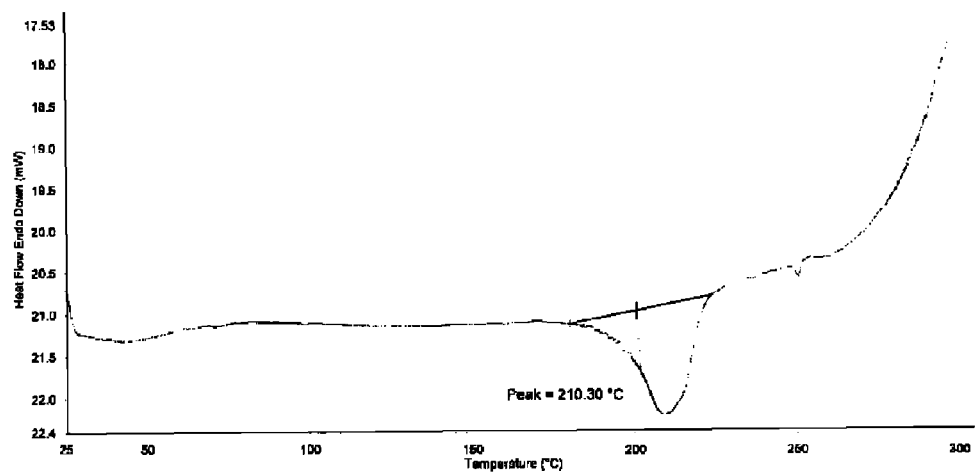

In a further aspect of the invention, crystalline form 4 of bosentan is characterized by a DSC comprising an endotherm at about 210° C. Preferably the crystalline form 4 of bosentan has a DSC substantially as depicted in FIG. 11.

Preferably the crystalline form 4 of bosentan of the present invention is substantially free of other polymorphic forms including amorphous bosentan. It preferably comprises less than 5%, preferably less than 3%, preferably less than 2%, preferably less than 1%, preferably less than 0.5%, preferably less than 0.1% of other polymorphic forms including amorphous bosentan.

There is also provided a process for preparing crystalline form 4 of bosentan comprising the steps of:
(a) dissolving bosentan in one or more organic solvent(s),
(b) causing a crystalline solid to precipitate from the solution obtained in step (a), and
(c) isolating the crystalline solid obtained in step (b).

Preferably the organic solvent in step (a) is isobutyl methyl ketone. Preferably at least 40%, more preferably at least 60%, most preferably at least 80% of the bosentan is dissolved in the organic solvent(s). In another embodiment the bosentan is dissolved by heating the organic solvent(s), preferably to about 50-100° C., more preferably to about 90° C. In a further embodiment still, in step (b) the crystalline solid is caused to precipitate by adding an anti-solvent. Alternatively, the crystalline solid is caused to precipitate by cooling the solution obtained in step (a), preferably the solution is cooled to about 5-30° C., preferably to about 10-30° C., preferably to about 25° C. In another embodiment, in step (c) the crystalline solid is isolated by filtration and preferably the crystalline solid is dried under vacuum or alternatively the crystalline solid is air-dried.

A further aspect of the invention provides amorphous bosentan.

Preferably the amorphous bosentan of the present invention is substantially free of other polymorphic forms. It preferably comprises less than 5%, preferably less than 3%, preferably less than 2%, preferably less than 1%, preferably less than 0.5%, preferably less than 0.1% of other polymorphic forms.

A further aspect of the invention provides a process for preparing amorphous bosentan comprising the steps of:
(a) dissolving bosentan in one or more organic solvent(s),
(b) causing an amorphous solid to precipitate from the solution obtained in step (a), and
(c) isolating the amorphous solid obtained in step (b).

In a particularly preferred embodiment, the organic solvent is t-butyl methyl ether. In another embodiment, preferably at least 40%, more preferably at least 60%, most preferably at least 80% of the bosentan is dissolved in the organic solvent(s). Preferably, the solution obtained in step (a) is heated to dissolve the bosentan, preferably to about 40-100° C., more preferably to about 52° C. In a further embodiment a co-solvent, preferably dichloromethane, is added to dissolve the bosentan. In a further embodiment, in step (b) the amorphous solid is caused to precipitate by adding one or more anti-solvent(s). In an alternative embodiment, in step (b) the solution is cooled to about 5-40° C., preferably to about 25° C., preferably over about 40 minutes. In a further embodiment, the amorphous solid obtained in step (c) is isolated by filtration and preferably is dried under vacuum, preferably for about 12 hours.

Further aspects of the invention provide pharmaceutical compositions comprising one of bosentan crystalline forms 1 to 4 or amorphous bosentan, and one or more pharmaceutically acceptable excipients, and the use of the pharmaceutical compositions for the treatment of an endothelin receptor mediated disorder. The receptor mediated disorder is preferably a cardiovascular disorder such as hypertension, pulmonary hypertension, ischemia, vasospasm and angina pectoris and in particular pulmonary arterial hypertension (PAH).

BRIEF DESCRIPTION OF THE ACCOMPANYING DRAWINGS

Figure 3:
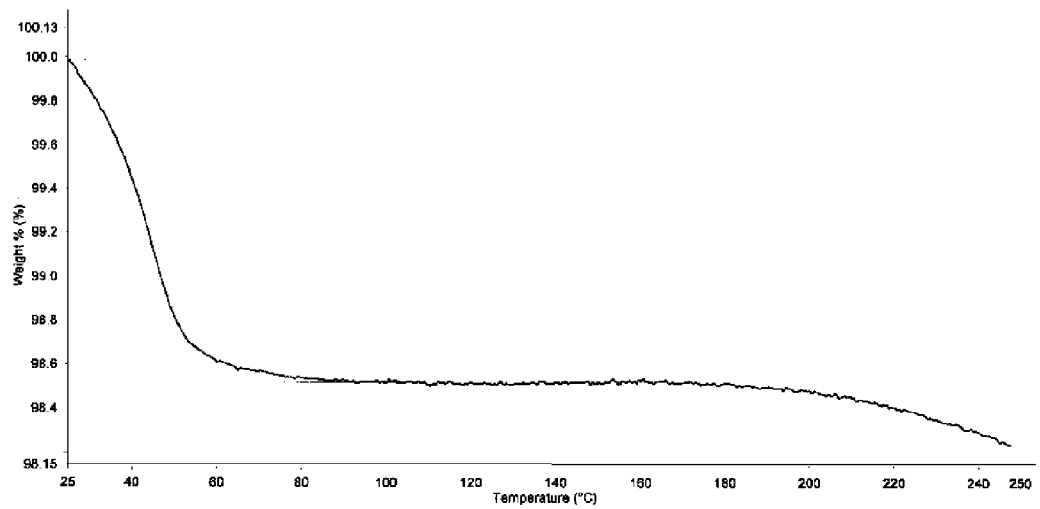
Figure 4:
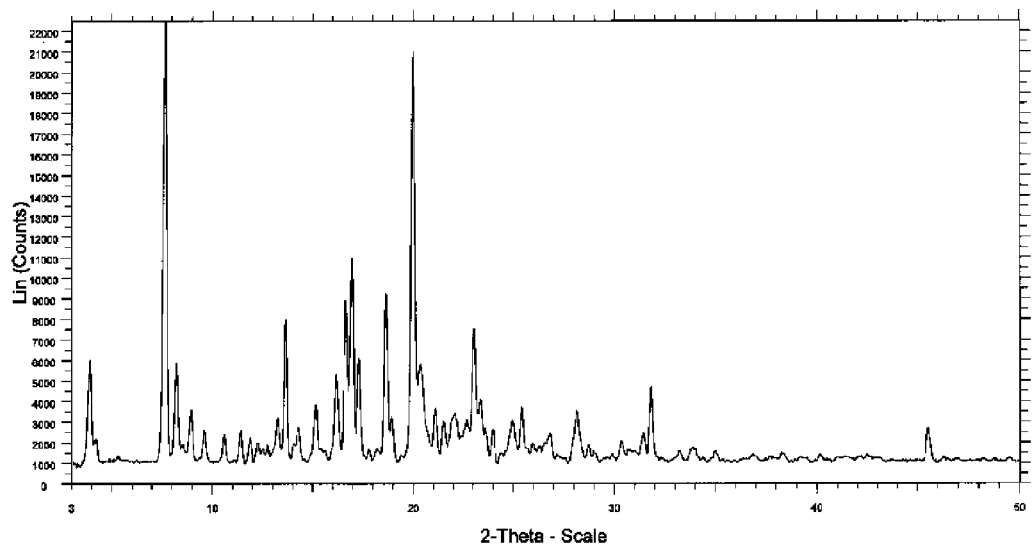
Figure 6:
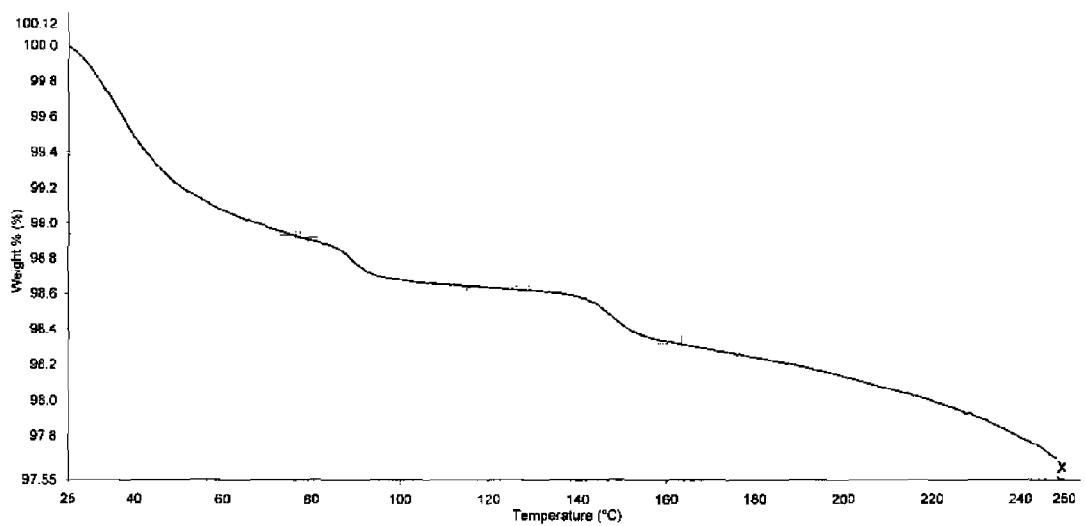
Figure 7:
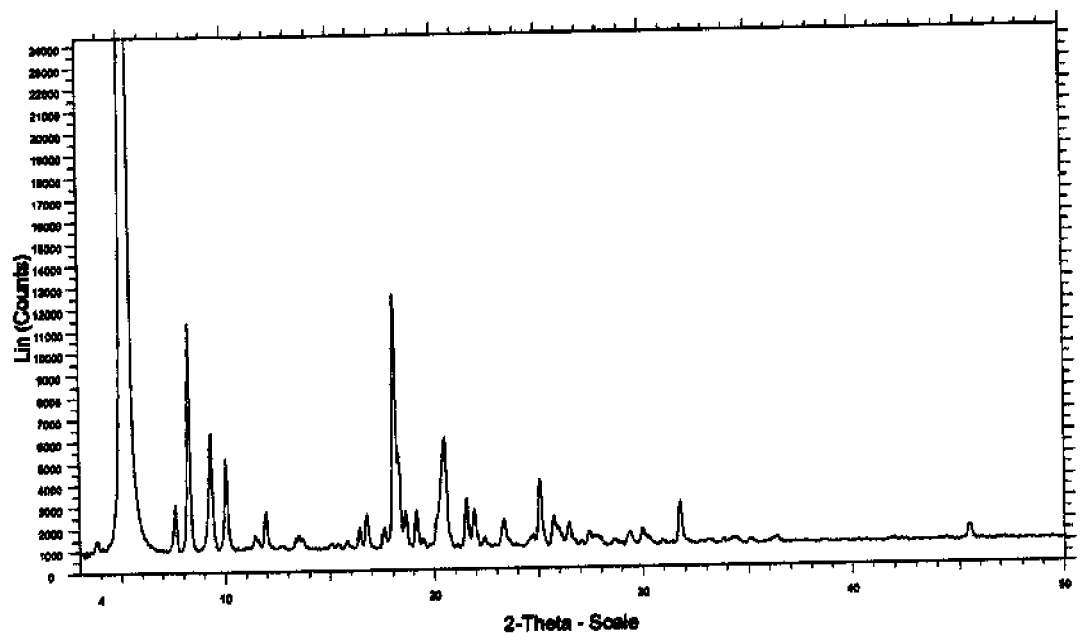
Figure 9:
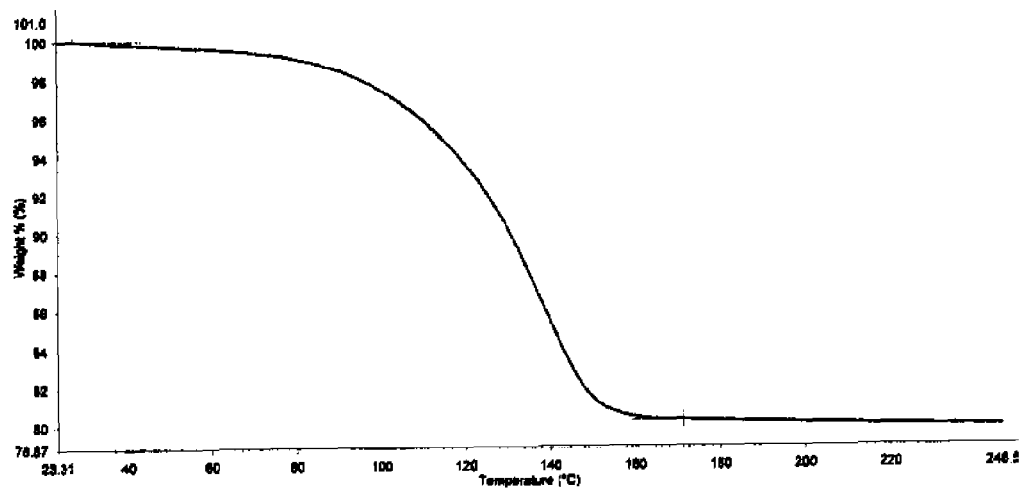
Figure 10:
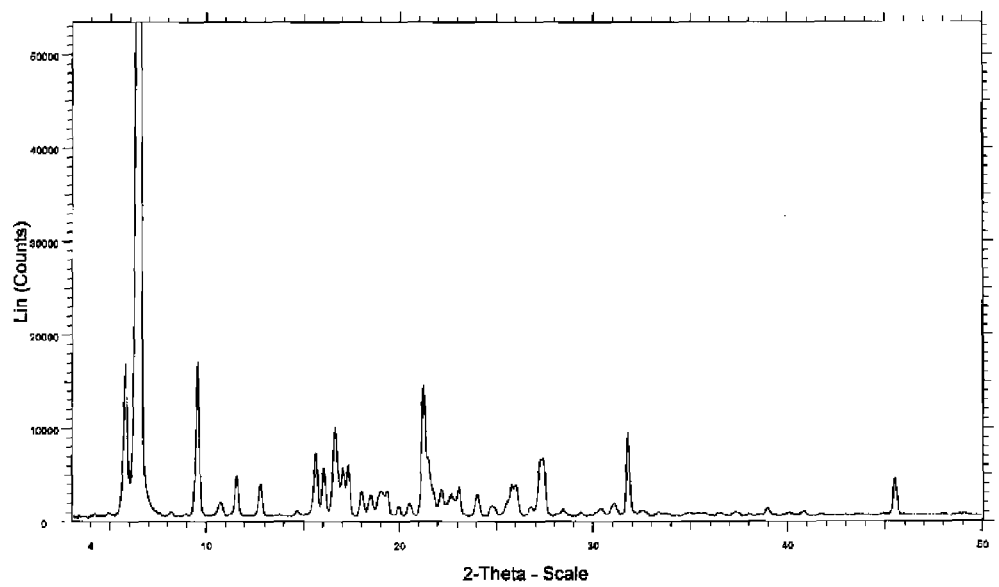
Figure 12:
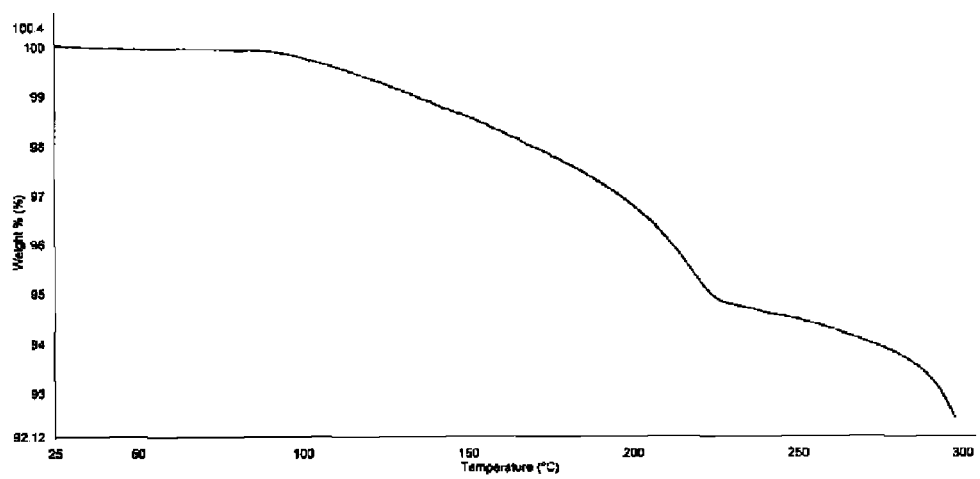
Figure 13:
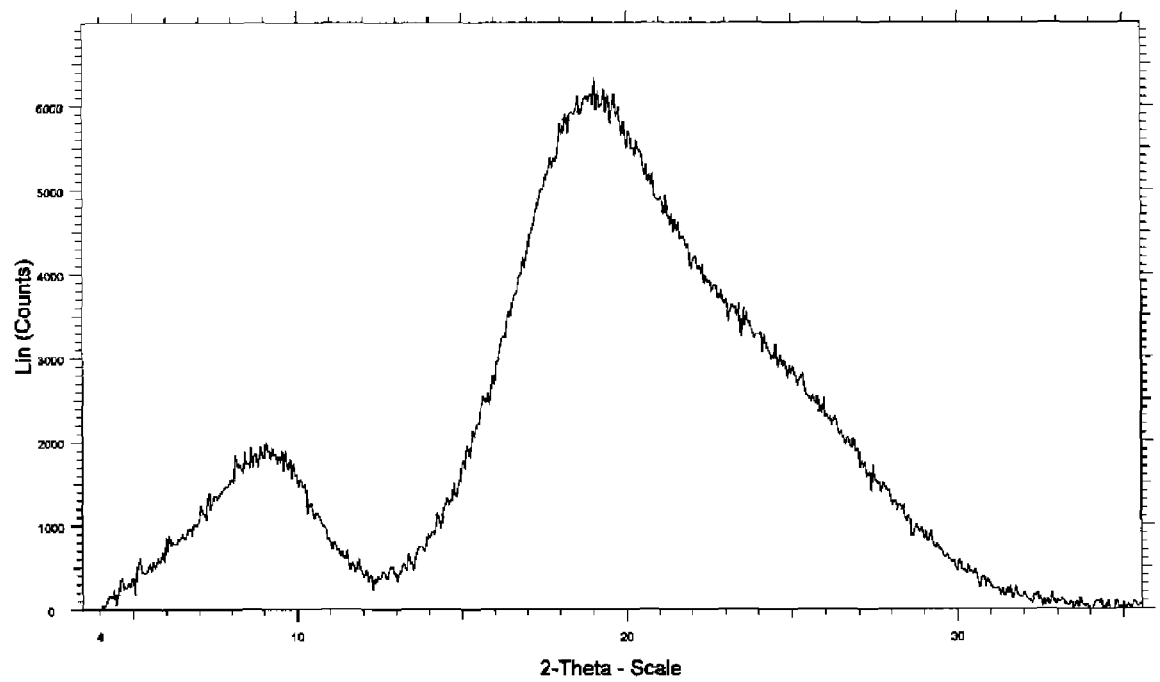

FIG. 1 describes the XRPD of bosentan form 1;
FIG. 2 describes the DSC of bosentan form 1;
FIG. 3 describes the TGA of bosentan form 1;
FIG. 4 describes the XRPD of bosentan form 2;
FIG. 5 describes the DSC of bosentan form 2
FIG. 6 describes the TGA of bosentan form 2;
FIG. 7 describes the XRPD of bosentan form 3;
FIG. 8 describes the DSC of bosentan form 3;
FIG. 9 describes the TGA of bosentan form 3;
FIG. 10 describes the XRPD of bosentan form 4;
FIG. 11 describes the DSC of bosentan form 4;
FIG. 12 describes the TGA of bosentan form 4;
FIG. 13 describes the XRPD of amorphous bosentan.

DETAILED DESCRIPTION OF THE INVENTION

The present invention provides novel crystalline forms 1 to 4 of bosentan and amorphous bosentan. The processes disclosed herein are capable of providing these novel polymorphic forms with consistent polymorphic purity irrespective of the scale of preparation. Further embodiments of the invention comprise compositions of these polymorphic forms along with one or more pharmaceutically acceptable excipient(s). Another aspect of the present invention is the use of these pharmaceutical compositions to treat patients suffering from cardiovascular disorders such as hypertension, ischemia, vasospasm, angina pectoris and pulmonary hypertension.

A further embodiment of the invention is a process for making a pharmaceutical composition comprising mixing a polymorphic form of bosentan according to the invention and one or more pharmaceutically acceptable excipients. In one embodiment of the invention, there is provided a method for the treatment of an endothelin receptor mediated disorder comprising administering to a subject in need thereof a composition comprising a therapeutically effective amount of a polymorphic form of bosentan according to the invention. In a further embodiment according to the invention, there is provided the use of a polymorphic form of bosentan according to the invention substantially free of other polymorphic forms, for the preparation of a medicament for treating an endothelin receptor mediated disorder in a subject in need thereof. Preferably the disorder is pulmonary hypertension.

In addition to the active ingredient(s), the pharmaceutical compositions of the present invention may contain one or more excipients. Excipients are added to the composition for a variety of purposes. Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. Carbopol®), carboxymethyl cellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminium silicate, maltodextrin, methyl cellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethyl cellulose calcium, carboxymethyl cellulose sodium (e.g. Ac-Di-Sol®, Primellose®), colloidal silicon dioxide, croscarmellose sodium, crospovidone (e.g. Kollidon®, Polyplasdone®), guar gum, magnesium aluminium silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions, the polymorphic form of bosentan and any other solid excipients are dissolved or suspended in a liquid carrier such as water, vegetable oil, alcohol, polyethylene glycol, propylene glycol or glycerine.

Liquid pharmaceutical compositions may further contain emulsifying agents to disperse uniformly throughout the composition an active ingredient or other excipient that is not soluble in the liquid carrier. Emulsifying agents that may be useful in liquid compositions include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions may also contain a viscosity enhancing agent to improve the mouth-feel or organoleptic qualities of the product and/or coat the lining of the gastrointestinal tract. Such agents include acacia, alginic acid, bentonite, carbomer, carboxymethyl cellulose calcium or sodium, cetostearyl alcohol, methyl cellulose, ethyl cellulose, gelatin, guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

A liquid composition may also contain a buffer such as gluconic acid, lactic acid, citric acid, acetic acid, sodium gluconate, sodium lactate, sodium citrate or sodium acetate.

Flavouring agents and flavour enhancers may make solid and liquid dosage forms more palatable to the patient. Common flavouring agents and flavour enhancers for pharmaceutical products that may be included in the composition include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxytoluene, butylated hydroxyanisole and ethylenediaminetetraacetic acid may be added at levels safe for ingestion to improve storage stability.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts. Dosage forms include solid dosage forms like tablets, powders, capsules, suppositories, sachets, troches and lozenges, as well as liquid syrups, suspensions and elixirs.

The dosage form of the present invention may be a capsule containing the composition, preferably a powdered or granulated solid composition of the invention, within either a hard or a soft shell. The shell may be made from gelatin and optionally contain a plasticizer such as glycerine and sorbitol, and an opacifying agent or colorant. The active ingredient and excipients may be formulated into compositions and dosage forms according to methods known in the art.

A composition for tabletting or capsule filling may be prepared by wet granulation. In wet granulation, some or all of the active ingredient and excipients in powder form are blended and then further mixed in the presence of a liquid, typically water, that causes the powders to clump into granules. The granulate is screened and/or milled, dried and then screened and/or milled to the desired particle size. The granulate may then be tabletted, or other excipients may be added prior to tabletting, such as a glidant and/or a lubricant.

A tabletting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a uniform tablet without granules. Excipients that are particularly well suited for direct compression tabletting include microcrystalline cellulose, spray dried lactose, dicalcium phosphate dihydrate and colloidal silica. The proper use of these and other excipients in direct compression tabletting is known to those in the art with experience and skill in particular formulation challenges of direct compression tabletting.

A capsule filling of the present invention may comprise any of the aforementioned blends and granulates that were described with reference to tabletting, however, they are not subjected to a final tabletting step.

In further embodiments, the composition of the invention may further comprise one or more additional active ingredients.

In the specification and in the claims, the terms "including" and "comprising" are open-ended terms and should be interpreted to mean "including, but not limited to.". These terms encompass the more restrictive terms "consisting essentially of" and "consisting of".

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following paragraphs enumerated consecutively from 1 through 83 provide for various aspects of the present invention. In one embodiment, in a first paragraph, the present invention provides:

1. Crystalline form 1 of bosentan characterized by an X-ray diffraction pattern comprising at least five peaks selected from peaks at 2θ values 3.9, 7.8, 8.8, 13.2, 16.1, 17.6, 18.7, 23.0 and 24.0±0.2.

2. Crystalline form 1 of bosentan characterized by a DSC comprising an endothermic peak at about 148° C.

3. A process for preparing the crystalline form 1 of bosentan as in paragraph 1 or 2, comprising the steps of:
(a) dissolving bosentan in one or more organic solvent(s),
(b) causing a crystalline solid to precipitate from the solution obtained in step (a), and
(c) isolating the crystalline solid obtained in step (b).

4. A process according to paragraph 3, wherein the organic solvent(s) in step (a) is/are selected from tetrahydrofuran, isobutanol, and ethanol.

5. A process according to paragraph 3 or 4, wherein in step (b) the crystalline solid is caused to precipitate by addition of one or more anti-solvent(s).

6. A process according to paragraph 5, wherein the anti-solvent is n-hexane or water.

7. A process according to any one of paragraphs 3-6, wherein in step (a) the organic solvent(s) is/are heated until at least 40% of the bosentan is dissolved in the organic solvent(s).

8. A process according to any one of paragraphs 3-7, wherein in step (a) the bosentan is dissolved in the organic solvent(s) by heating the organic solvent(s) to a temperature that facilitates the bosentan dissolving.

9. A process according to any one of paragraphs 3-8, wherein the solution obtained in step (a) is filtered.

10. A process according to paragraph 9, wherein an anti-solvent is added to the filtrate.

11. A process for preparing the crystalline form 1 of bosentan as in paragraph 1 or 2, comprising the steps of:
(a) heating bosentan in isobutanol until a clear solution is obtained,
(b) cooling the solution obtained in step (a),
(c) filtering the solution obtained in step (b),
(d) adding one or more anti-solvent(s) to the filtrate obtained in step (c),
(e) isolating the crystalline solid obtained in step (d), and
(f) drying the crystalline solid obtained in step (e).

12. A process according to paragraph 11, wherein the anti-solvent used in step (d) is n-hexane.

13. A process for preparing the crystalline form 1 of bosentan as in paragraph 1 or 2, comprising the steps of:
(a) dissolving bosentan in tetrahydrofuran at room temperature until a clear solution is obtained,
(b) adding one or more anti-solvent(s) to the solution obtained in step (a),
(c) isolating the crystalline solid obtained in step (b), and
(d) drying the crystalline solid obtained in step (c).

14. A process according to paragraph 13, wherein the anti-solvent used in step (b) is n-hexane.

15. Crystalline form 2 of bosentan characterized by an X-ray diffraction pattern comprising at least five peaks selected from peaks at 2θ values 7.6, 13.6, 16.6, 16.9, 17.3, 18.6, 20.0, 20.3 and 23.0±0.2.

16. Crystalline form 2 of bosentan characterized by a DSC comprising an endothermic peak at about 144° C.

17. A process for preparing the crystalline form 2 of bosentan as in paragraph 15 or 16, comprising the steps of:
(a) dissolving bosentan in one or more organic solvent(s),
(b) causing a crystalline solid to precipitate from the solution obtained in step (a), and
(c) isolating the crystalline solid obtained in step (b).

18. A process according to paragraph 17, wherein the organic solvent(s) in step (a) is/are selected from n-butanol, 2-ethoxyethanol, n-propyl acetate, and 2-methoxyethanol.

19. A process according to paragraph 17 or 18, wherein at least 40% of the bosentan is dissolved in the organic solvent(s).

20. A process according to any one of paragraphs 17-19, wherein the organic solvent in step (a) is n-butanol.

21. A process according to paragraph 20, wherein the bosentan is dissolved by heating the n-butanol.

22. A process according to paragraph 20 or 21, wherein in step (b) the crystalline solid is caused to precipitate by adding one or more anti-solvent(s).

23. A process according to paragraph 22, wherein the anti-solvent is n-hexane.

24. A process according to any one of paragraphs 17-19, wherein the organic solvent in step (a) is 2-ethoxyethanol.

25. A process according to paragraph 24, wherein the bosentan is dissolved by heating the 2-ethoxyethanol.

26. A process according to paragraph 24 or 25, wherein in step (b) the crystalline solid is caused to precipitate by adding one or more anti-solvent(s).

27. A process according to paragraph 26, wherein the anti-solvents are n-hexane and water.

28. A process according to any one of paragraphs 17-19, wherein the organic solvent in step (a) is 2-methoxyethanol.

29. A process according to paragraph 28, wherein the bosentan is dissolved by heating the 2-methoxyethanol.

30. A process according to paragraph 28 or 29, wherein the crystalline solid is caused to precipitate by cooling the solution obtained in step (a).

31. A process for preparing the crystalline form 2 of bosentan as in paragraph 15 or 16, comprising the steps of:
(a) heating bosentan in n-butanol to about 90° C.,
(b) cooling the solution obtained in step (a) to about 25° C. over about 60 minutes,
(c) filtering the solution obtained in step (b),
(d) adding n-hexane to the filtrate obtained in step (c) to precipitate a crystalline solid,
(e) isolating the crystalline solid obtained in step (d) by filtration, and
(f) air-drying the crystalline solid obtained in step (e) for about 12 hours.

32. A process for preparing the crystalline form 2 of bosentan as in paragraph 15 or 16, comprising the steps of:
(a) heating bosentan in 2-ethoxyethanol to about 45° C.,
(b) cooling the solution obtained in step (a) to about 10° C. over about 50 minutes,
(c) adding n-hexane and water to the solution obtained in step (b) to precipitate a crystalline solid,
(d) isolating the crystalline solid obtained in step (c) by filtration, and
(e) air-drying the crystalline solid obtained in step (d) for about 12 hours.

33. A process for preparing the crystalline form 2 of bosentan as in paragraph 15 or 16, comprising the steps of:
(a) heating bosentan in n-propyl acetate to about 80° C.,
(b) cooling the solution obtained in step (a) to about 25° C. to precipitate a crystalline solid,
(c) isolating the crystalline solid obtained in step (b) by filtration, and
(d) air-drying the crystalline solid obtained in step (c) for about 12 hours.

34. A process for preparing the crystalline form 2 of bosentan as in paragraph 15 or 16, comprising the steps of:
(a) heating bosentan in 2-methoxyethanol to about 45° C. or until a clear solution is obtained,
(b) cooling the solution obtained in step (a) to about 25° C.,
(c) adding water to the solution obtained in step (b) to precipitate a crystalline solid,
(d) isolating the crystalline solid obtained in step (c) by filtration, and
(e) air-drying the crystalline solid obtained in step (d) for about 12 hours.

35. Crystalline form 3 of bosentan characterized by an X-ray diffraction pattern comprising at least five peaks selected from peaks at 2θ values 5.2, 7.5, 8.2, 9.3, 10.0, 18.1, 20.5, 21.5 and 25.0±0.2.

36. Crystalline form 3 of bosentan characterized by a DSC comprising an endothermic peak at about 174° C. and an endothermic peak at about 246° C.

37. A process for preparing the crystalline form 3 of bosentan as in paragraph 35 or 36, comprising the steps of:
(a) dissolving bosentan in one or more organic solvent(s),
(b) causing a crystalline solid to precipitate from the solution obtained in step (a), and
(c) isolating the crystalline solid obtained in step (b).

38. A process according to paragraph 37, wherein the organic solvent(s) comprise(s) an alcoholic solvent.

39. A process according to paragraph 38, wherein the organic solvent(s) comprise(s) a straight or branched chain $C_1$-$C_6$ alcohol.

40. A process according to paragraph 39, wherein the organic solvent(s) is/are selected from n-pentanol, isoamyl alcohol, cyclohexanol, n-propanol, n-butanol, cyclopentanol, and isobutanol.

41. A process according to paragraph 37, wherein the organic solvent is cyclohexane.

42. A process according to paragraph 37, wherein the organic solvent is toluene.

43. A process according to any one of paragraphs 37-42, wherein at least 40% of the bosentan is dissolved in the organic solvent(s).

44. A process according to any one of paragraphs 37-43, wherein the bosentan is dissolved by heating the organic solvent(s).

45. A process according to any one of paragraphs 37-44, wherein in step (b) the crystalline solid is caused to precipitate by adding one or more anti-solvent(s).

46. A process according to paragraph 45, wherein when the organic solvent is n-pentanol, the anti-solvent is n-hexane.

47. A process according to paragraph 45, wherein when the organic solvent is toluene, the anti-solvent is water.

48. A process according to any one of paragraphs 37-47, wherein the crystalline solid is caused to precipitate by cooling the solution obtained in step (a).

49. Crystalline form 4 of bosentan characterized by an X-ray diffraction pattern comprising at least five peaks selected from peaks at 2θ values 5.7, 6.4, 9.5, 15.6, 16.6, 21.2, 21.5, 27.4 and 31.8±0.2.

50. Crystalline form 4 of bosentan characterized by a DSC comprising an endothermic peak at about 210° C.

51. A process for preparing the crystalline form 4 of bosentan as in paragraph 49 or 50, comprising the steps of:
(a) dissolving bosentan in one or more organic solvent(s),
(b) causing a crystalline solid to precipitate from the solution obtained in step (a), and
(c) isolating the crystalline solid obtained in step (b).

52. A process according to paragraph 51, wherein the organic solvent in step (a) is isobutyl methyl ketone.

53. A process according to paragraph 51 or 52, wherein at least 40% of the bosentan is dissolved in the organic solvent(s).

54. A process according to any one of paragraphs 51-53, wherein the bosentan is dissolved by heating the organic solvent(s).

55. A process according to any one of paragraphs 51-54, wherein in step (b) the crystalline solid is caused to precipitate by adding one or more anti-solvent(s).

56. A process according to any one of paragraphs 51-55, wherein the crystalline solid is caused to precipitate by cooling the solution obtained in step (a).

57. Amorphous bosentan.

58. A process for preparing amorphous bosentan, comprising the steps of:
(a) dissolving bosentan in one or more organic solvent(s),
(b) causing an amorphous solid to precipitate from the solution obtained in step (a), and
(c) isolating the amorphous solid obtained in step (b).

59. A process according to paragraph 58, wherein the organic solvent is t-butyl methyl ether.

60. A process according to paragraph 58 or 59, wherein at least 40% of the bosentan is dissolved in the organic solvent(s).

61. A process according to any one of paragraphs 58-60, wherein the bosentan is dissolved by heating the organic solvent(s).

62. A process according to any one of paragraphs 58-61, wherein in step (b) the amorphous solid is caused to precipitate by adding one or more anti-solvent(s).

63. A pharmaceutical composition comprising bosentan crystalline form 1 as in paragraph 1 or 2 and one or more pharmaceutically acceptable excipients.

64. A pharmaceutical composition comprising bosentan crystalline form 2 as in paragraph 15 or 16 and one or more pharmaceutically acceptable excipients.

65. A pharmaceutical composition comprising bosentan crystalline form 3 as in paragraph 35 or 36 and one or more pharmaceutically acceptable excipients.

66. A pharmaceutical composition comprising bosentan crystalline form 4 as in paragraph 49 or 50 and one or more pharmaceutically acceptable excipients.

67. A pharmaceutical composition comprising amorphous bosentan and one or more pharmaceutically acceptable excipients.

68. Bosentan crystalline form 1 as in paragraph 1 or 2, for treating or preventing an endothelin receptor mediated disorder.

69. Bosentan crystalline form 2 as in paragraph 15 or 16, for treating or preventing an endothelin receptor mediated disorder.

70. Bosentan crystalline form 3 as in paragraph 35 or 36, for treating or preventing an endothelin receptor mediated disorder.

71. Bosentan crystalline form 4 as in paragraph 49 or 50, for treating or preventing an endothelin receptor mediated disorder.

72. Amorphous bosentan, for treating or preventing an endothelin receptor mediated disorder.

73. Bosentan according to any one of paragraphs 68-72, wherein the endothelin receptor mediated disorder is a cardiovascular disorder.

74. Bosentan according to paragraph 73, wherein the cardiovascular disorder is hypertension, pulmonary hypertension, ischemia, vasospasm or angina pectoris.

75. Bosentan according to paragraph 73, wherein the cardiovascular disorder is pulmonary arterial hypertension.

76. A method of treating or preventing an endothelin receptor mediated disorder, comprising administering a therapeutically or prophylactically effective amount of bosentan crystalline form 1 as in paragraph 1 or 2 to a subject in need thereof.

77. A method of treating or preventing an endothelin receptor mediated disorder, comprising administering a therapeutically or prophylactically effective amount of bosentan crystalline form 2 as in paragraph 15 or 16 to a subject in need thereof.

78. A method of treating or preventing an endothelin receptor mediated disorder, comprising administering a therapeutically or prophylactically effective amount of bosentan crystalline form 3 as in paragraph 35 or 36 to a subject in need thereof.

79. A method of treating or preventing an endothelin receptor mediated disorder, comprising administering a therapeutically or prophylactically effective amount of bosentan crystalline form 4 as in paragraph 49 or 50 to a subject in need thereof.
80. A method of treating or preventing an endothelin receptor mediated disorder, comprising administering a therapeutically or prophylactically effective amount of amorphous bosentan to a subject in need thereof
81. A method according to any one of paragraphs 76-80, wherein the endothelin receptor mediated disorder is a cardiovascular disorder.
82. A method according to paragraph 81, wherein the cardiovascular disorder is hypertension, pulmonary hypertension, ischemia, vasospasm or angina pectoris.
83. A method according to paragraph 81, wherein the cardiovascular disorder is pulmonary arterial hypertension.

The details of the invention, its objects and advantages are explained hereunder in greater detail in relation to non-limiting exemplary illustrations.

EXAMPLES

Examples 1-3

Methods for Preparing Bosentan Form 1

Example 1

Bosentan was added to ethanol (3 vol) at reflux temperature (not a clear solution) and water (3 vol) added dropwise. The suspension was stirred at 25° C. for 6 hours and filtered. The solid product was dried at 25-30° C. under vacuum for 12 hours. XRPD and DSC analysis data confirmed that the product obtained was bosentan form 1.

Example 2

Bosentan was heated in isobutanol (2 vol) to 90° C. (clear solution), cooled to 30° C. and filtered. To the filtrate was added n-hexane (20 vol) and the precipitated solid was filtered and air-dried for 12 hours. XRPD and DSC analysis data confirmed that the product obtained was bosentan form 1.

Example 3

Bosentan was dissolved in tetrahydrofuran (5 vol) at 25° C. (clear solution) and n-hexane (40 vol) was added to precipitate a solid. The solid was filtered and dried under vacuum at 25° C. for 12 hours. XRPD and DSC analysis data confirmed that the product obtained was bosentan form 1.

Examples 4-7

Methods for Preparing Bosentan Form 2

Example 4

Bosentan was heated in n-butanol (5 vol) to 90° C. (not a clear solution), cooled to 25° C. within 60 minutes and filtered. To the filtrate was added n-hexane (20 vol) to precipitate a solid. The solid was filtered and air-dried. XRPD and DSC analysis data confirmed that the product obtained was bosentan form 2.

Example 5

Bosentan was heated in 2-ethoxyethanol (2 vol) to 45° C. (clear solution) and cooled to 10° C. within 50 minutes. n-Hexane (5 vol) and water (5 vol) were added to precipitate a solid which was then filtered. The filtered solid was air-dried for 12 hours. XRPD and DSC analysis data confirmed that the product obtained was bosentan form 2.

Example 6

Bosentan was heated in n-propyl acetate (3 vol) to 81° C. (clear solution) and cooled to 25° C. within 60 minutes. The resultant solid was filtered and air-dried for 12 hours. XRPD and DSC analysis data confirmed that the product obtained was bosentan form 2.

Example 7

Bosentan was heated in 2-methoxyethanol (2 vol) to 43° C. (clear solution) and cooled to 25° C. within 60 minutes. Water (3 vol) was added to precipitate a solid which was then filtered. The filtered solid was air-dried for 12 hours. XRPD and DSC analysis data confirmed that the product obtained was bosentan form 2.

Examples 8-17

Methods for Preparing Bosentan Form 3

Example 8

Bosentan was heated in n-pentanol (3 vol) to 83° C. (clear solution), cooled to 30° C. and filtered. To the filtrate was added n-hexane (7 vol) and the precipitated solid was filtered and air-dried for 12 hours. XRPD and DSC analysis data confirmed that the product obtained was bosentan form 3.

Example 9

Bosentan was heated in isoamyl alcohol (4 vol) to 45° C. (clear solution) and cooled to 12° C. within 80 minutes. The resultant solid was filtered and dried under vacuum at 25° C. for 12 hours. XRPD and DSC analysis data confirmed that the product obtained was bosentan form 3.

Example 10

Bosentan was heated in cyclohexanol (2 vol) to 44° C. (clear solution) and cooled to 9° C. within 60 minutes. The resultant solid was filtered and dried under vacuum at 25° C. for 12 hours. XRPD and DSC analysis data confirmed that the product obtained was bosentan form 3.

Example 11

Bosentan was heated in n-propanol (2 vol) to 48° C. (clear solution) and cooled to 7° C. within 60 minutes. The resultant solid was filtered and dried under vacuum at 25° C. for 12 hours. XRPD and DSC analysis data confirmed that the product obtained was bosentan form 3.

Example 12

Bosentan was heated in n-butanol (5 vol) to 90° C. (clear solution) and cooled to 25° C. within 80 minutes. The resultant solid was filtered and dried under vacuum at 25° C. for 12 hours. XRPD and DSC analysis data confirmed that the product obtained was bosentan form 3.

Example 13

Bosentan was heated in cyclopentanol (2 vol) to 50° C. (clear solution) and cooled to 25° C. within 70 minutes. The resultant solid was filtered and dried under vacuum at 25° C. for 12 hours. XRPD and DSC analysis data confirmed that the product obtained was bosentan form 3.

Example 14

Bosentan was heated in isobutanol (2 vol) to 50° C. (clear solution) and cooled to 25° C. within 4 hours. The resultant solid was filtered and dried under vacuum at 25° C. for 12 hours. XRPD and DSC analysis data confirmed that the product obtained was bosentan form 3.

Example 15

Bosentan was heated briefly in n-butanol (5 vol) to 90° C. (not a clear solution) and cooled to 25° C. within 60 minutes. The resultant solid was filtered and dried under vacuum at 25° C. for 12 hours. XRPD and DSC analysis data confirmed that the product obtained was bosentan form 3.

Example 16

Bosentan was heated in cyclohexane (60 vol) to 70° C. (not a clear solution). Dichloromethane (30 vol) was added to obtain a clear solution, which was cooled to 25° C. within 3 hours. The resultant solid was filtered and dried under vacuum at 25° C. for 12 hours. XRPD and DSC analysis data confirmed that the product obtained was bosentan form 3.

Example 17

Bosentan was heated in toluene (30 vol) to 60° C. (clear solution) and cooled to 25° C. within 60 minutes. Water (15 vol) was added. After 2 hours the resultant solid was filtered and dried under vacuum at 25° C. for 12 hours. XRPD and DSC analysis data confirmed that the product obtained was bosentan form 3.

Example 18

Method for Preparing Bosentan Form 4

Example 18

Bosentan was heated in isobutyl methyl ketone (20 vol) to 90° C. (clear solution) and cooled to 25° C. After 2 hours the resultant solid was filtered and dried under vacuum at 25° C. for 12 hours. XRPD and DSC analysis data confirmed that the product obtained was bosentan form 3.

Example 19

Method for preparing amorphous bosentan

Example 19

Bosentan was heated in t-butyl methyl ether (5 vol) to 52° C. (not a clear solution). Dichloromethane (20 vol) was added to obtain a clear solution. The solution was cooled to 25° C. within 40 minutes. After 2 hours the resultant solid was filtered and dried under vacuum at 25° C. for 12 hours. XRPD and DSC analysis data confirmed that the product obtained was amorphous bosentan.

It will be understood that the present invention has been described above by way of example only. The examples are not intended to limit the scope of the invention. Various modifications and embodiments can be made without departing from the scope and spirit of the invention, which is defined by the following claims only.

What is claimed is:

1. Crystalline form 2 of bosentan characterized by:
   (i) an X-ray diffraction pattern comprising at least five peaks selected from peaks at 2θ values 7.6, 13.6, 16.6, 16.9, 17.3, 18.6, 20.0, 20.3 and 23.0±0.2; and/or
   (ii) a DSC comprising an endothermic peak at about 144° C.

2. A process for preparing the crystalline form 2 of bosentan as claimed in claim 1, comprising the steps of:
   (a) dissolving bosentan in one or more organic solvent(s),
   (b) causing a crystalline solid to precipitate from the solution obtained in step (a), and
   (c) isolating the crystalline solid obtained in step (b).

3. A process for preparing the crystalline form 2 of bosentan as claimed in claim 1, comprising the steps of:
   (a) heating bosentan in n-butanol to about 90° C.,
   (b) cooling the solution obtained in step (a) to about 25° C. over about 60 minutes,
   (c) filtering the solution obtained in step (b),
   (d) adding n-hexane to the filtrate obtained in step (c) to precipitate a crystalline solid,
   (e) isolating the crystalline solid obtained in step (d) by filtration, and
   (f) air-drying the crystalline solid obtained in step (e) for about 12 hours.

4. A process for preparing the crystalline form 2 of bosentan as claimed in claim 1, comprising the steps of:
   (a) heating bosentan in 2-ethoxyethanol to about 45° C.,
   (b) cooling the solution obtained in step (a) to about 10° C. over about 50 minutes,
   (c) adding n-hexane and water to the solution obtained in step (b) to precipitate a crystalline solid,
   (d) isolating the crystalline solid obtained in step (c) by filtration, and
   (e) air-drying the crystalline solid obtained in step (d) for about 12 hours.

5. A process for preparing the crystalline form 2 of bosentan as claimed in claim 1, comprising the steps of:
   (a) heating bosentan in n-propyl acetate to about 80° C.,
   (b) cooling the solution obtained in step (a) to about 25° C. to precipitate a crystalline solid,
   (c) isolating the crystalline solid obtained in step (b) by filtration, and
   (d) air-drying the crystalline solid obtained in step (c) for about 12 hours.

6. A process for preparing the crystalline form 2 of bosentan as claimed in claim 1, comprising the steps of:
   (a) heating bosentan in 2-methoxyethanol to about 45° C. or until a clear solution is obtained,
   (b) cooling the solution obtained in step (a) to about 25° C.,
   (c) adding water to the solution obtained in step (b) to precipitate a crystalline solid,
   (d) isolating the crystalline solid obtained in step (c) by filtration, and
   (e) air-drying the crystalline solid obtained in step (d) for about 12 hours.

7. Crystalline form 3 of bosentan characterized by:
   (i) an X-ray diffraction pattern comprising at least five peaks selected from peaks at 2θ values 5.2, 7.5, 8.2, 9.3, 10.0, 18.1, 20.5, 21.5 and 25.0±0.2; and/or
   (ii) a DSC comprising an endothermic peak at about 174° C. and an endothermic peak at about 246° C.

8. A process for preparing the crystalline form 3 of bosentan as claimed in claim 7, comprising the steps of:

(a) dissolving bosentan in one or more organic solvent(s),
(b) causing a crystalline solid to precipitate from the solution obtained in step (a), and
(c) isolating the crystalline solid obtained in step (b).

9. Crystalline form 4 of bosentan characterized by:
(i) an X-ray diffraction pattern comprising at least five peaks selected from peaks at 2θ values 5.7, 6.4, 9.5, 15.6, 16.6, 21.2, 21.5, 27.4 and 31.8±0.2;
(ii) a DSC comprising an endothermic peak at about 210° C.

10. A process for preparing the crystalline form 4 of bosentan as claimed in claim 9, comprising the steps of:
(a) dissolving bosentan in one or more organic solvent(s),
(b) causing a crystalline solid to precipitate from the solution obtained in step (a), and
(c) isolating the crystalline solid obtained in step (b).

11. Amorphous bosentan.

12. A process for preparing amorphous bosentan as claimed in claim 11, comprising the steps of:
(a) dissolving bosentan in one or more organic solvent(s),
(b) causing an amorphous solid to precipitate from the solution obtained in step (a), and
(c) isolating the amorphous solid obtained in step (b).

13. A method of treating hypertension, ischemia, vasospasm, angina pectoris, and pulmonary arterial hypertension comprising administering a therapeutically effective amount of bosentan crystalline form 2 as claimed in claim 1 to a subject in need thereof.

14. A method of treating hypertension, ischemia, vasospasm, angina pectoris, and pulmonary arterial hypertension comprising administering a therapeutically effective amount of bosentan crystalline form 3 as claimed in claim 7 to a subject in need thereof.

15. A method of treating hypertension, ischemia, vasospasm, angina pectoris, and pulmonary arterial hypertension comprising administering a therapeutically effective amount of bosentan crystalline form 4 as claimed in claim 9 to a subject in need thereof.

16. A method of treating hypertension, ischemia, vasospasm, angina pectoris, and pulmonary arterial hypertension comprising administering a therapeutically effective amount of amorphous bosentan as claimed in claim 11 to a subject in need thereof.

\* \* \* \* \*